United States Patent [19]

Hauel et al.

[11] Patent Number: 4,699,909

[45] Date of Patent: Oct. 13, 1987

[54] BENZOTRIAZOLYL-4,5-DIHYDRO-3(2H)-PYRIDAZINONES

[75] Inventors: Norbert Hauel; Volkhard Austel, both of Biberach; Joachim Heider, Warthausen; Manfred Reiffen, Biberach; Willi Diederen, Biberach; Walter Haarman, Biberach, all of Fed. Rep. of Germany

[73] Assignee: Dr. Karl Thomae GmbH, Biberach an der Riss, Fed. Rep. of Germany

[21] Appl. No.: 889,814

[22] Filed: Jul. 24, 1986

Related U.S. Application Data

[60] Division of Ser. No. 749,580, Jun. 27, 1985, Pat. No. 4,616,018, which is a continuation of Ser. No. 656,081, Sep. 28, 1984, abandoned, which is a continuation of Ser. No. 568,270, Jan. 5, 1984, abandoned, which is a continuation of Ser. No. 397,590, Jul. 12, 1982, abandoned.

[30] Foreign Application Priority Data

Jul. 25, 1981 [DE] Fed. Rep. of Germany ......... 129447

[51] Int. Cl.⁴ .................... C07D 403/02; A61K 31/50
[52] U.S. Cl. ..................................... 514/254; 544/238
[58] Field of Search .......................... 544/238; 514/254

[56] References Cited

U.S. PATENT DOCUMENTS 4,026,891  5/1977  Austel et al. .................... 544/238 X
4,258,185  3/1981  Nakao et al. ................... 544/238 X
4,361,563  11/1982  Austel et al. .................... 544/238 X Primary Examiner—Donald G. Daus
Assistant Examiner—William A. Teoli, Jr
Attorney, Agent, or Firm—Weissenberger, Hammond & Littell

[57] ABSTRACT

Compounds of the formula

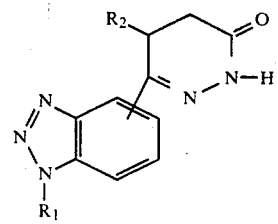

wherein $R_1$ is hydrogen; alkyl of 1 to 7 carbon atoms; cycloalkyl of 3 to 7 carbon atoms; monosubstituted alkyl of 1 to 3 carbon atoms, where the substituent is pyridyl, methypyridyl, phenyl, mono-, di- or trisubstituted phenyl, where the substituents on the phenyl ring, which may be identical to or different from each other, are selected from the group consisting of one amino, one dimethylamino, one to two hydroxyls, one to three methoxys and one to three halogens; ω-monosubstituted alkyl of 2 to 4 carbon atoms, where the substituent is hydroxyl or di(alkyl of 1 to 3 carbon atoms)amino; phenyl; monohalo-phenyl; unsubstituted or monosubstituted straight or branched alkanoyl of 1 to 6 carbon atoms, where the substituent is phenyl, methoxyphenyl or cycloalkyl of 3 to 7 carbon atoms; or unsubstituted or monosubstituted phenylsulfonyl, where the substituent is methyl or methoxy; and $R_2$ is hydrogen or alkyl of 1 to 3 carbon atoms;

and non-toxic, pharmacologically acceptable acid addition salts thereof. The compounds as well as their salts are useful as cardiotonics, hypotensives and antithrombotics.

7 Claims, No Drawings

BENZOTRIAZOLYL-4,5-DIHYDRO-3(2H)-PYRIDAZINONES

This is a division of Ser. No. 749,580, filed June 27, 1985, now U.S. Pat. No. 4,616,018, which in turn is a continuation of application Ser. No. 656,081, filed Sept. 28, 1984, now abandoned; which in turn is a continuation of application Ser. No. 568,270 filed Jan. 5, 1984, now abandoned; which in turn is a continuation of application Ser. No. 397,590, filed July 12, 1982, now abandoned.

This invention relates to novel benzotriazolyl-dihydropyridazinones and salts thereof, to methods of preparing these compounds, to pharmaceutical compositions containing them as active ingredients, and to methods of using them as cardiotonics, hypotensives and antithrombotics.

More particularly, the present invention relates to a novel class of compounds represented by the formula

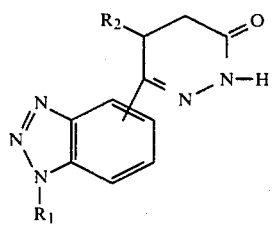

wherein
$R_1$ is hydrogen; alkyl of 1 to 7 carbon atoms; cycloalkyl of 3 to 7 carbon atoms; monosubstituted alkyl of 1 to 3 carbon atoms, where the substituent is pyridyl, methylpyridyl, phenyl, or mono-, di- or trisubstituted phenyl, where the substituents on the phenyl ring, which may be identical to or different from each other, are selected from the group consisting of one amino, one dimethylamino, one to two hydroxyls, one to three methoxys and one to three halogens; ω-monosubstituted alkyl of 2 to 4 carbon atoms, where the substituent is hydroxyl or di(alkyl of 1 to 3 carbon atoms)amino; phenyl; monohalo-phenyl; unsubstituted or monosubstituted straight or branched alkanoyl of 1 to 6 carbon atoms, where the substituent is phenyl, methoxyphenyl or cycloalkyl of 3 to 7 carbon atoms; or unsubstituted or monosubstituted phenylsulfonyl, where the substituent is methyl or methoxy; and
$R_2$ is hydrogen or alkyl of 1 to 3 carbon atoms;
and non-toxic, pharmacologically acceptable addition salts thereof formed with inorganic or organic acids.

Specific examples of substituents $R_1$ and $R_2$ in formula I are the following:

$R_1$—Hydrogen, methyl, ethyl, propyl, isopropyl, butyl, isobutyl, tert.butyl, pentyl, isopentyl, neopentyl, tert. pentyl, hexyl, heptyl, cyclopropyl, cyclobutyl, cyclopentyl, cyclohexyl, cycloheptyl, benzyl, 1-phenylethyl, 2-phenylethyl, 1-phenylpropyl, 2-phenylpropyl, 3-phenylpropyl, pyridylmethyl, methylpyridylmethyl, 2-pyridylethyl- 3-(methylpyridyl)propyl, aminobenzyl, dimethylaminobenzyl, methoxybenzyl, dimethoxybenzyl, trimethoxybenzyl, hydroxybenzyl, dihydroxybenzyl, fluorobenzyl, difluorobenzyl, chlorobenzyl, dichlorobenzyl, trichlorobenzyl, bromobenzyl, dibromobenzyl, aminodichlorobenzyl, aminodibromobenzyl, dimethylamino-dichlorobenzyl, dimethylamino-dibromobenzyl, hydroxydichlorobenzyl, hydrocydibromobenzyl, methoxychlorobenzyl, methoxydichlorobenzyl, methoxybromobenzyl, methoxydibromobenzyl, 2-(methoxyphenyl)-ethyl, 2-(dimethoxyphenyl)ethyl, 2-(chlorophenyl)-ethyl, 3-(methoxyphenyl)propyl, 3-(fluorophenyl)-propyl, 3-(bromophenyl)propyl, 2-hydroxyethyl, 3-hydroxypropyl, 4-hydroxybutyl, 2-aminoethyl, 3-aminopropyl, 4-aminobutyl, 2-dimethylaminoethyl, 2-dipropylaminoethyl, 3-dipropylaminopropyl, 4-dimethylaminobutyl, 4-diethylaminobutyl, 4-dipropylaminobutyl, phenyl, fluorophenyl, chlorophenyl, bromophenyl, formyl, acetyl, propionyl, butanoyl, pentanoyl, hexanoyl, dimethylacetyl, benzoyl, methoxybenzoyl, phenyldimethylacetyl, cyclopropanoyl, cyclopentanoyl, cyclohexanoyl, cycloheptanoyl, phenylacetyl, 3-phenylpropionyl, 4-phenylbutanoyl, phenylsulfonyl, methylphenylsulfonyl or methoxyphenylsulfonyl group; and $R_2$—hydrogen, methyl, ethyl, propyl or isopropyl.

A preferred subgenus is constituted by those compounds of the formula I wherein
$R_1$ is hydrogen; alkyl of 1 to 6 carbon atoms; cycloalkyl of 3 to 6 carbon atoms; benzyl; hydroxybenzyl; dimethylamino-benzyl; mono- or dimethoxy-benzyl; amino-dichloro-benzyl; amino-dibromo-benzyl; α-monosubstituted alkyl of 2 to 4 carbon atoms, where the substituent is hydroxyl, methoxyphenyl or di(alkyl of 1 to 3 carbon atoms)amino; alkanoyl of 1 to 6 carbon atoms; phenyl-(alkanoyl of 1 to 6 carbon atoms); methoxyphenyl-(alkanoyl of 1 to 6 carbon atoms); pyridylmethyl; methylpyridylmethyl; phenyl; fluorophenyl; chlorophenyl; bromophenyl; cyclohexanoyl; or methoxyphenylsulfonyl; and
$R_2$ is hydrogen or methyl;
and non-toxic, pharmacologically acceptable acid addition salts thereof, especially those where the pyridazinone ring is attached to the 5-position of the benzotriazole moiety.

An especially preferred subgenus is constituted by compounds of the formula

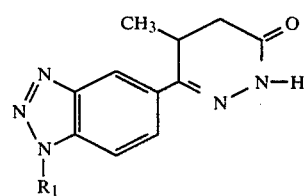

wherein
$R_1$ is alkyl of 1 to 4 carbon atoms, dimethylaminoethyl, cyclohexanoyl, p-methoxy-benzoyl or p-methoxy-benzyl,
and non-toxic, pharmacologically acceptable addition salts thereof.

The compounds embraced by formula I may be prepared by the following methods:

METHOD A

By reacting a compound of the formula

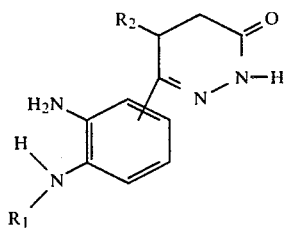

wherein

R₁ and R₂ have the meanings previously defined, with an inorganic or organic nitrite.

The reaction is advantageously performed in a suitable solvent, for instance with an inorganic nitrite such as sodium nitrite in water, water/methanol or water/dioxane, and in the presence of an acid such as hydrochloric, sulfuric or glacial acetic acid, but preferably in semi-concentrated hydrochloric acid as the solvent, or with an organic nitrite such as an ester of nitrous acid, for example ethyl nitrite or tert. butyl nitrite, in methanol, ethanol or dioxane, at low temperatures, for instance at temperatures between $-10°$ and $40°$ C., but preferably at temperatures between $0°$ and $25°$ C.

METHOD B

By reacting a carboxylic acid of the formula

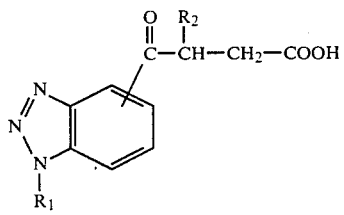

wherein $R_1$ and $R_2$ have the meanings previously defined, or an anhydride, ester, thioester, amide, imidazolide or halide thereof, with hydrazine.

The reaction is advantageous carried out in a solvent such as methanol, ethanol, isopropanol, glacial acetic acid or propionic acid and/or in an excess of hydrazine or hydrazine hydrate at temperatures between $0°$ and $200°$ C., for instance at temperatures between $20°$ and $150°$ C., but preferably at the boiling point of the reaction mixture, and optionally in the presence of an acid such as sulfuric acid or p-toluenesulfonic acid as a condensation agent. However, the reaction may also be carried out without a solvent.

The compounds of the formula I wherein R₂ is other than hydrogen comprise an optically active carbon atom in the 5-position of the pyridazinone ring and can be separated into their optically active enantiomers by cleavage of the racemates.

Cleavage of the racemates is advantageously effected by fractional crystallization of the corresponding salts with optionally active acids, such as tartaric, dibenzoyltartaric, malic, camphoric or camphorsulfonic acid, or by chromatography on optically active adsorbents.

The compounds embraced by formula I are basic and therefore form addition salts with inorganic or organic acids. Examples of non-toxic, pharmacologically acceptable acid addition salts are those formed with hydrochloric acid, hydrobromic acid, sulfuric acid, phosphoric acid, fumaric acid, succinic acid, lactic acid, citric acid, tartaric acid, maleic acid or the like.

The starting compounds of the formula II and III may be prepared by methods described in the literature. For example, a compound of the formula II is obtained by reacting a corresponding substituted 3-(nitroaminobenzoyl)-propionic acid ester with hydrazine and subsequently reducing the nitro group.

A compound of the formula III is obtained by reacting a compound of the formula

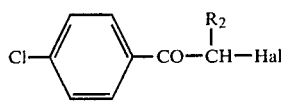

with a malonic acid ester. The compound thus obtained is then hydrolyzed, decarboxylated and nitrated, the chlorine atom is replaced by a corresponding amino group, the resulting amino compound is optionally alkylated or acylated, the nitro group is reduced, and the resulting intermediate is cyclized with a nitrite to form the desired triazole.

The following examples illustrate the present invention and will enable others skilled in the art to understand it more completely. It should be understood, however, that the invention is not limited solely to the particular examples given below.

PREPARATION OF STARTING COMPOUNDS

EXAMPLE I

5-Methyl-6-[3'-nitro-4'-benzylamino-phenyl]-4,5-dihydro-3(2H)-pyridazinone 10.9 gm (40.0 mmols) of 3-methyl-4-oxo-4-(3'-nitro-4'-chloro-phenyl)-butyric acid and 21.4 gm (200.0 mmols) of benzylamine were dissolved in 100 ml of ethanol, and the solution was refluxed for 5 hours. Then, the solvent was evaporated in vacuo, and the residue was added to a mixture of 500 ml of ice-cold water and 50 ml of concentrated hydrochloric acid, whereupon an oily product precipitated. After being separated from the aqueous phase and without prior purification, this oil was heated for one hour at $110°$ C. in a solution of 20 ml of 99% hydrazine hydrate and 100 ml of glacial acetic acid. The reaction mixture was then stirred into 200 ml of water, and the precipitated product was suction-filtered off, washed with water and dried at $80°$ C.

Yield: 13.4 gm (99% of theory).

Melting point: $187°–191°$ C.

$C_{18}H_{18}N_4O_3$ (338.37): Calc.: C-63.89%; H-5.36%; N-16.56%. Found: C-64.58%; H-5.48%; N-16.22%.

EXAMPLE II

5-Methyl-6-[3'-amino-4'-benzylamino-phenyl]-4,5-dihydro-3(2H)-pyridazinone 12.5 gm (36.9 mmols) of 5-methyl-6-[3'-nitro-4'-benzylamino-phenyl]-4,5-dihydro-3(2H)-pyridazinone were added to a mixture of 20 ml of 99% hydrazine hydrate and 350 ml of ethanol, and then 10 gm of Raney nickel were added. After 24 hours' stirring at room temperature, the solid components were suction-filtered off, dissolved in dimethyl formamide, the catalyst was filtered off, and the filtrate was evaporated. The crystalline residue thus obtained was digested with ethanol, washed with ether and dried.

Yield: 9.5 gm (82.5% of theory).
Melting point: 186°–188° C.

EXAMPLE III

3-Methyl-4-oxo-4-[3'-nitro-4'-(4-dimethylamino-butylamino)phenyl]-butyric acid 4 gm (14.75 mmols) of 3-methyl-4-oxo-4-(3'-nitro-4'-chlorophenyl)-butyric acid and 5.8 gm (50.0 mmols) of 4-dimethylaminobutyl-amine were refluxed in 50 ml of ethanol for 2 hours, and then the volatile components were evaporated in vacuo. A viscous oil was obtained, which was reacted further without being purified.

Yield: 5.18 gm (100% of theory).

Thin-layer chromatogram: $R_f = 0.12$ (silicagel, eluant: methylene chloride/ethanol = 19:1).

EXAMPLE IV

3-Methyl-4-oxo-4-[3'-amino-4'-(4-dimethylamino-butylamino)phenyl]-butyric acid 5.18 gm (about 14.75 mmols) of crude 3-methyl-4-oxo-4-[3'-nitro-4'-(4-dimethylaminobutyl-amino)-phenyl]-butyric acid were dissolved in 50 ml of methanol and, after the addition of 1 gm of Raney nickel, treated in a Parr apparatus at room temperature with hydrogen (5 bars). After the calculated amount of hydrogen had been taken up, the reaction was stopped, the catalyst was removed from the reaction mixture, and the filtrate was evaporated in vacuo. The reaction product thus obtained was reacted further without being purified.

Yield: 4.8 gm (100% of theory).

Thin-layer chromatogram: $R_f = 0.19$ (silicagel, eluant: ethanol).

EXAMPLE V

3-Methyl-4-oxo-4-[1'-(4-dimethylamino-butyl)-benzotriazol-5'-yl]-butyric acid 4.8 gm (about 14.7 mmols) of cryde 3-methyl-4-oxo-4-[3'-amino-4'-(4-dimethylamino-butylamino)-phenyl]-butyric acid were dissolved in 100 ml of 2N hydrochloric acid, and at 0° to 5° C. a solution of 1.38 gm (20 mmols) of sodium nitrite in 10 ml of water was added dropwise thereto. After being stirred for two hours at room temperature the reaction mixture was evaporated to dryness in vacuo. The crude product thus obtained was reacted further without being purified.

Yield: 5.3 gm of crude product.

Thin-layer chromatogram: $R_f = 0.38$ (silicagel, eluant: ethanol).

EXAMPLE VI

Methyl 3-methyl-4-oxo-4-[3'-nitro-4'-(α-methyl-α-phenyl-propionylamino)]-butyrate 6 gm (22.5 mmols) of methyl 3-methyl-4-oxo-4-(3'-nitro-4'-amino-phenyl)-butyrate were refluxed with 9 ml of α-methyl-α-phenyl-propionic acid chloride in 50 ml of chlorobenzene for 8 hours. Then, the solvent was evaporated in vacuo, and the reaction product was obtained from the residue as a yellow oil by column chromatography (800 gm of silica gel, methylene chloride).

Yield: 9.25 gm (100% of theory).

Thin-layer chromatogram: $R_f = 0.73$ (silica gel, eluant: methylene chloride/ethanol = 19:1).

EXAMPLE VII

5-Methyl-6-[3'-nitro-4'-(α-methyl-α-phenyl-propionylamino)phenyl]-4,5-dihydro-3(2H)-pyridazinone 9 gm (21.8 mmols) of methyl 3-methyl-4-oxo-4-[3'-nitro-4'-(α-methyl-α-phenyl-propionylamino)]-butyrate were heated at 110° C. for 1½ hours in a solution of 20 ml of 99% hydrazine hydrate in 100 ml of glacial acetic acid. The mixture was then poured into 200 ml of ice-cold water. The reaction product which precipitated was suction-filtered off, dried and purified by column chromatography (500 gm of silica gel, methylene chloride with 0.5% of ethanol).

Yield: 7.0 gm (79% of theory).

Melting point: 160°–162° C.

$C_{21}H_{22}N_4O_4$ (394.4): Calc.: C-63.95%; H-5.62%; N-14.20%. Found: C-64.05%; H-5.65%; N-14.51%.

EXAMPLE VIII

5-Methyl-6-[3'-amino-4'-(α-methyl-α-phenyl-propionylamino)-phenyl]-4,5-dihydro-3(2H)-pyridazinone 6.78 gm (17.2 mmols) of 5-methyl-6-[3'-nitro-4'-(α-methyl-α-phenyl-propionylamino)-phenyl]-4, 5-dihydro-3(2H)-pyridazinone were dissolved in 80 ml of dimethylformamide and, after the addition of 1 gm of 10% palladium-on-charcoal, the mixture was treated with hydrogen (5 bars) in a Parr apparatus at room temperature. After the uptake of hydrogen was complete, the catalyst was filtered off, and the filtrate was concentrated by evaporation in vacuo. The crude product thus obtained as an oily residue was reacted further without being purified.

Yield: 6.3 gm (about 100% of theory).

Thin-layer chromatogram: $R_f = 0.55$ (silica gel, eluant: methylene chloride/ethanol = 9:1).

PREPARATION OF THE END PRODUCTS OF THE FORMULA 1

EXAMPLE 1

5-Methyl-6-(1'-benzyl-benzotriazol-5'-yl)-4,5-dihydro-3(2H)-pyridazinone 9 gm (29.2 mmols) of 5-methyl-6-(3'-amino-4'-benzylamino-phenyl)-4,5-dihydro-3(2H)-pyridazinone were dissolved in 200 ml of semi-concentrated hydrochloric acid, and at 0° to 5° C. a solution of 4.13 gm (60 mmols) of sodium nitrite in 40 ml of water was slowly added dropwise, while stirring. After the reaction mixture had been stirred for another 5 hours at room temperature, the reaction product was suction-filtered off and recrystallized from acetone.

Yield: 6.5 gm (69.6% of theory).

Melting point: 160°–162° C.

$C_{18}H_{17}N_5O$ (319.4): Calc.: C-67.70%; H-5.37%; N-21.93% Found: C-67.52%; H-5.45%; N-21.56%.

EXAMPLE 2

5-Methyl-6-[1'-(4-dimethylamino-butyl)-benzotriazol-5'-yl]-4,5-dihydro-3(2H)-pyridazinone 5.3 gm (about 14 mmols) of crude 3-methyl-4-oxo-4-[1'-(4-dimethylamino-butyl)-benzotriazol-5'-yl]-butyric acid were added to a solution of 15 ml of 99% hydrazine hydrate in 50 ml of glacial acetic acid, and the mixture was heated at 110° C. for 2 hours and then poured into 150 ml of water. The aqueous solution was made slightly alkaline with 2N ammonia and was extracted several times with methylene chloride. After drying over sodium sulfate, the combined organic extracts were evaporated to dryness in vacuo. The crude product thus obtained was purified by column chromatography (300 gm of silica gel, methylene chloride +10% ethanol).

Yield: 1.4 gm (28.8% of theory).
Melting point: 134°–136° C.
$C_{17}H_{24}N_6O$ (328.43): Calculated: C-62.17%; H-7.37%; N-25.59%. Found: C-61.23%; H-7.35%; N-25.38%.

EXAMPLE 3

5-Methyl-6-(benzotriazol-5'-yl)-4,5-dihydro-3(2H)-pyridazinone

This compound was prepared analogous to Example 1 from 5-methyl-6-(3', 4'-diamino-phenyl)-4,5-dihydro-3(2H)-pyridazinone.

Yield: 39.5% of theory.
Melting point: 247°–249° C.
$C_{11}H_{11}N_5O$ (229.2): Calculated: C-57.63%; H-4.84%; N-30.55%. Found: C-57.40%; H-4.90%; N-30.31%.

EXAMPLE 4

5-Methyl-6-(1'-methylbenzotriazol-5'-yl)-4,5-dihydro-3(2H)-pyridazinone

This compound was prepared analogous to Example 1 from 5-methyl-6-(3'-amino-4'-methylamino-phenyl)-4,5-dihydro-3(2H)-pyridazinone.

Yield: 29.4% of theory.
Melting point: 223°–224° C.
$C_{12}H_{13}N_5O$ (243.3): Calculated: C-59.25%; H-5.39%; N-28.79%. Found: C-59.13%; H-5.60%; N-29.28%.

EXAMPLE 5

5-Methyl-6-(1'-ethyl-benzotriazol-5'-yl)-4,5-dihydro-3(2H)-pyridazinone

This compound was prepared analogous to Example 1 from 5-methyl-6-(3'-amino-4'-ethylamino-phenyl)-4,5-dihydro-3(2H)-pyridazinone.

Yield: 29.5% of theory.
Melting point: 189°–192° C.
$C_{13}H_{15}N_5O$ (257.3): Calculated: C-60.69%; H-5.88%; N-27.22%. Found: C-60.60%; H-5.86%; N-27.41%.

EXAMPLE 6

5-Methyl-6-(1'-isopropyl-benzotriazol-5'-yl)-4,5-dihydro-3(2H)-pyridazinone

This compound was prepared analogous to Example 1 from 5-methyl-6-(3'-amino-4'-isopropylamino-phenyl)-4,5-dihydro-3(2H)-pyridazinone.

Yield: 51.3% of theory.
Melting point: 185°–187° C.
$C_{14}H_{17}N_5O$ (271.3): Calculated: C-61.98%; H-6.32%; N-25.81%. Found: C-62.03%; H-6.26%; N-25.69.

EXAMPLE 7

5-Methyl-6-(1'-cyclopropyl-benzotriazol-5'-yl)-4,5-dihydro-3(2H)-pyridazinone

This compound was prepared analogous to Example 1 from 5-methyl-6-(3'-amino-4'-cyclopropylamino-phenyl)-4,5-dihydro-3(2H)-pyridazinone.

Yield: 39.5% of theory.
Melting point: 219°–221° C.
$C_{14}H_{15}N_5O$ (269.3): Calculated: C-62.44%; H-5.61%; N-26.00%. Found: C-62.91%; H-5.61%; N-26.44%.

EXAMPLE 8

5-Methyl-6-(1'-n-hexyl-benzotriazol-5'-yl)-4,5-dihydro-3(2H)-pyridazinone

This compound was prepared analogous to Example 1 from 5-methyl-6-(3'-amino-4'-n-hexylamino-phenyl)-4,5-dihydro-3(2H)-pyridazinone.

Yield: 38.2% of theory.
Melting point: 162°–164° C.
$C_{17}H_{23}N_5O$ (313.4): Calculated: C-65.15%; H-7.40%; N-22.35%. Found: C-65.30%; H-7.16%; N-22.48.

EXAMPLE 9

5-Methyl-6-[1'(2-hydroxy-ethyl)-benzotriazol-5'-yl]-4,5-dihydro-3(2H)-pyridazinone This compound was prepared analogous to Example 1 from 5-methyl-6-[3'-amino-4'-(2-hydroxyethyl)amino-phenyl]-4,5-dihydro-3(2H)-pyridazinone.

Yield: 26% of theory.
Melting point: 182°–183° C. $C_{13}H_{15}N_5O$ (273.3): Calculated: C-57.13%; H-5.53%; N-25.63%. Found: C-57.00%; H-5.50%; N-25.60%.

EXAMPLE 10

5-Methyl-6-[1'-(2-dimethylamino-ethyl)-benzotriazol-5'-yl]-4,5-dihydro-3(2H)-pyridazinone This compound was prepared analogous to Example 1 from 5-methyl-6-(3'-amino-4'-dimethylaminoethylamino-phenyl)-4,5-dihydro-3(2H)-pyridazinone.

Yield: 32% of theory.
Melting point: 146°–148° C.
$C_{15}H_{20}N_6O$ (300.37): Calculated: C-59.98%; H-6.71%; N-27.98%. Found: C-60.07%; H-6.70%; N-28.09%.

EXAMPLE 11

5-Methyl-6-[1'-(3-di-n-propylamino-propyl)-benzotriazol-5'-yl]-4,5-dihydro-3(2H)-pyridazinone This compound was prepared analogous to Example 1 from 5-methyl-6-[3'-amino-4'-(3-di-n-propylaminopropyl-amino)phenyl]-4,5-dihydro-3 (2H)-pyridazinone.

Yield: 11% of theory.
Melting point: 142°–144° C.
$C_{20}H_{30}N_6O$ (370.51): Calculated: C-64.84%; H-8.16%; N-22.68%. Found: C-65.28%; H-7.96%; N-22.63%.

EXAMPLE 12

5-Methyl-6-(1'-cyclohexyl-benzotriazol-5'-yl)-4,5-dihydro-3(2H)-pyridazinone

This compound was prepared analogous to Example 1 from 5-methyl-6-(3'-amino-4'-cyclohexylamino-phenyl)-4,5-dihydro-3(2H)-pyridazinone.

Yield: 64% of theory.
Melting point: 212°–213° C.
$C_{17}H_{21}N_5O$ (309.4): Calculated: C-65.57%; H-6.80%; N-22.49%. Found: C-65.12%; H-6.70%; N-22.47%.

EXAMPLE 13

5-Methyl-6-(1'-phenyl-benzotriazol-5'-yl)-4,5-dihydro-3(2H)-pyridazinone

This compound was prepared analogous to Example 1 from 5-methyl-6-(3'-amino-4'-phenylamino-phenyl)-4,5-dihydro-3(2H)-pyridazinone.

Yield: 38.4% of theory.

Melting point: 218°–219° C.

$C_{17}H_{15}N_5O$ (305.3): Calculated: C-66.87%; H-4.95%; N-22.94%. Found: C-66.51%; H-4.94%; N-22.77%.

EXAMPLE 14

5-Methyl-6-(1'-p-fluorophenyl-benzotriazol-5'-yl)-4,5-dihydro-3(2H)-pyridazinone This compound was prepared analogous to Example 1 from 5-methyl-6-(3'-amino-4'-p-fluorophenylamino-phenyl)-4,5-dihydro-3(2H)-pyridazinone.

Yield: 58% of theory.

Melting point: >250° C.

$C_{17}H_{14}N_5OF$ (323.34): Calculated: C-63.14%; H-4.36%; N-21.66%. Found: C-63.20%; H-4.51%; N-21.59%.

EXAMPLE 15

5-Methyl-6-(1'-p-methoxybenzyl-benzotriazol-5'-yl)-4,5-dihydro-3(2H)-pyridazinone This compound was prepared analogous to Example 1 from 5-methyl-6-(3'-amino-4'-p-methoxybenzylamino-phenyl)-4,5-dihydro-3(2H)-pyridazinone.

Yield: 14.3% of theory.

Melting point: 157°–159° C.

$C_{19}H_{19}N_5O_2$ (349.4): Calculated: C-65.32%; H-5.48%; N-20.04%. Found: C-65.40%; H-5.55%; N-20.01%.

EXAMPLE 16

5-Methyl-6-(1'-p-hydroxybenzyl-benzotriazol-5'-yl)-4,5-dihydro-3(2H)-pyridazinone This compound was prepared analogous to Example 1 from 5-methyl-6-(3'-amino-4'-p-hydroxybenzylamino-phenyl)-4,5-dihydro-3(2H)-pyridazinone.

Yield: 26.9% of theory.

Melting point: 193°–195° C.

$C_{18}H_{17}N_5O_2$ (335.4): Calculated: C-64.47%; H-5.11%; N-20.88%. Found: C-64.48%; H-5.22%; N-21.16%.

EXAMPLE 17

5-Methyl-6-{1'-[2-(p-methoxy-phenyl)-ethyl]-benzotriazol-5'-yl}-4,5-dihydro-3(2H)-pyridazinone This compound was prepared analogous to Example 1 from 5-methyl-6-{3'-amino-4'-[2-(p-methoxy-phenyl)-ethyl-amino]phenyl}-4, 5-dihydro-3(2H)-pyridazinone.

Yield: 20.8% of theory.

Melting point: 218°–220° C.

$C_{20}H_{21}N_5O_2$ (363.4): Calculated: C-66.10%; H-5.82%; N-19.27%. Found: C-66.24%; H-5.71%; N-19.27%.

EXAMPLE 18

5-Methyl-6-[1'-(3,4-dimethoxy-benzyl)-benzotriazol-5'-yl]-4,5-dihydro-3(2H)-pyridazinone This compound was prepared analogous to Example 1 from 5-methyl-6-[3'-amino-4'-(3,4-dimethoxybenzyl-amino)-phenyl]-4,5-dihydro-3(2H)-pyridazinone.

Yield: 52% of theory.

Melting point: 197°–200° C.

$C_{20}H_{21}N_5O_3$ (379.4): Calculated: C-63.31%; H-5.58%; N-18.40%. Found: C-63.37%; H-5.46%; N-18.29%.

EXAMPLE 19

5-Methyl-6-(1'-p-dimethylaminobenzyl-benzotriazol-5'-yl)-4,5-dihydro-3(2H)-pyridazinone This compound was prepared analogous to Example 1 from 5-methyl-6-(3'-amino-4'-p-dimethylaminobenzylamino-phenyl)-4,5-dihydro-3(2H)-pyridazinone.

Yield: 35% of theory.

Melting point: 196°–198° C.

$C_{20}H_{22}N_6O$ (362.44): Calculated: C-66.27%; H-6.12%; N-23.18%. Found: C-65.52%; H-6.29%; N-23.64%.

EXAMPLE 20

5-Methyl-6-(1'-p-methoxyphenylsulfonyl-benzotriazol-5'-yl)-4,5-dihydro-3(2H)-pyridazinone This compound was prepared analogous to Example 1 from 5-methyl-6-(3'-amino-4'-p-methoxyphenylsulfonylamino-phenyl)-4,5-dihydro-3(2H)-pyridazinone.

Yield: 33% of theory.

Melting point: 170°–173° C.

$C_{18}H_{17}N_5O_4S$ (399.44): Calculated: C-54.12%; H-4.29%; N-17.53%; S-8.03%. Found: C-54.20%; H-4.38%; N-17.85%; S-8.13%.

EXAMPLE 21

5-Methyl-6-[1'-(2-picolyl)-benzotriazol-5'-yl]-4,5-dihydro-3(2H)-pyridazinone

This compound was prepared analogous to Example 1 from 5-methyl-6-[3'-amino-4'-(2-picolylamino)-phenyl]-4,5-dihydro-3(2H)-pyridazinone.

Yield: 39.7% of theory.

Melting point: 95°–97° C.

$C_{17}H_{16}N_6O$ (320.36): Calculated: C-63.74%; H-5.03%; N-26.24%. Found: C-63.04%; H-5.43%; N-26.93%.

EXAMPLE 22

5-Methyl-6-[1'-(3-picolyl)-benzotriazol-5'-yl]-4,5-dihydro-3(2H)-pyridazinone

This compound was prepared analogous to Example 1 from 5-methyl-6-[3'-amino-4'-(2-picolylamino)-phenyl]-4,5-dihydro-3(2H)-pyridazinone.

Yield: 39.8% of theory.

Melting point: 202°–204° C.

$C_{17}H_{16}N_6O$ (320.36): Calculated: C-63.74%; H-5.03%; N-26.24%. Found: C-63.95%; H-5.14%; N-26.39%.

EXAMPLE 23

5-Methyl-6-[1'-(6-methyl-2-picolyl)-benzotriazol-5'-yl]-4,5-dihydro-3(2H)-pyridazinone This compound was prepared analogous to Example 1 from 5-methyl-6-[3'-amino-4'-(6-methyl-2-picolylamino)-phenyl]-4,5-dihydro-3(2H)-pyridazinone.

Yield: 40% of theory.

Melting point of the hydrochloride: 213°–218° C.

$C_{18}H_{18}N_6O \times HCl$ (370.85): Calculated: C-58.30%; H-5.16%; N-22.66%; Cl-9.56%. Found: C-58.37%; H-5.01%; N-23.29%; Cl-9.71%.

EXAMPLE 24

5-Methyl-6-[1'-(3,5-dichloro-4-amino-benzyl)-benzotriazol-5'-yl]-4,5-dihydro-3(2H)-pyridazinone This compound was prepared analogous to Example 1 from 5-methyl-6-[3'-amino-4'-(3,4-dichloro-4-amino-benzyl-amino)-phenyl]-4,5-dihydro-3(2H)-pyridazinone.

Yield: 10.5% of theory.
Melting point: 250°–252° C.
$C_{18}H_{18}N_6OCl_2$ (401.27).

EXAMPLE 25

5-Methyl-6-[1'-(α-methyl-α-phenyl-propionyl)-benzotriazol-5'-yl]-4,5-dihydro-3(2H)-pyridazinone This compound was prepared analogous to Example 1 from 5-methyl-6-[3'-amino-4'-(α-methyl-α-phenyl-propionyl-amino)-phenyl]-4,5-dihydro-3(2H)-pyridazinone.

Yield: 36.4% of theory.
Melting point: 196°–198° C.
$C_{21}H_{21}N_5O_2$ (375.4): Calculated: C-67.18%; H-5.64%; N-18.65%. Found: C-67.00%; H-5.66%; N-18.65%.

EXAMPLE 26

5-Methyl-6-(1'-acetyl-benzotriazol-5'-yl)-4,5-dihydro-3(2H)-pyridazinone

This compound was prepared analogous to Example 1 from 5-methyl-6-(3'-amino-4'-acetylamino-phenyl)-4,5-dihydro-3(2H)-pyridazinone.

Yield: 8.0% of theory.
Melting point: 213°–215° C.

EXAMPLE 27

5-Methyl-6-(1'-n-hexanoyl-benzotriazol-5'-yl)-4,5-dihydro-3(2H)-pyridazinone

This compound was prepared analogous to Example 1 from 5-methyl-6-(3'-amino-4'-n-hexanoylamino-phenyl)-4,5-dihydro-3(2H)-pyridazinone.

Yield: 55.5% of theory.
Melting point: 147°–149° C.
$C_{17}H_{21}N_5O_2$ (327.4): Calculated: C-62.37%; H-6.47%; N-21.39%. Found: C-62.43%; H-6.42%; N-21.38%.

EXAMPLE 28

5-Methyl-6-(1'-p-methoxybenzoylbenzotriazol-5'-yl)-4,5-dihydro-3(2H)-pyridazinone This compound was prepared analogous to Example 1 from 5-methyl-6-(3'-amino-4'-p-methoxybenzoylamino-phenyl)-4,5-dihydro-3(2H)-pyridazinone.

Yield: 61.3% of theory.
Melting point: 220°–225° C.
$C_{19}H_{17}N_5O_3$ (363.4): Calculated: C-62.80%; H-4.72%; N-19.27%. Found: C-62.98%; H-4.84%; N-19.37%.

EXAMPLE 29

5-Methyl-6-(1'-cyclohexanoyl-benzotriazol-5'-yl)-4,5-dihydro-3(2H)-pyridazinone

This compound was prepared analogous to Example 1 from 5-methyl-6-(1'-amino-4'-cyclohexanoylamino-phenyl)-4,5-dihydro-3(2H)-pyridazinone.

Yield: 76.3% of theory.
Melting point: 218°–221° C.
$C_{18}H_{21}N_5O_2$ (339.4): Calculated: C-63.70%; H-6.24%; N-20.63%. Found: C-64.13%; H-6.11%; N-20.45%.

The compounds of the present invention, that is, those embraced by formula I above and their non-toxic, pharmacologically acceptable acid addition salts, have useful pharmacodynamic properties. More particularly, they exhibit cardiovascular properties, namely cardiotonic, hypotensive and antithrombotic activities in warm-blooded animals such as rats.

The above pharmacological properties of the compounds of the present invention were ascertained by the standard test methods described below, and the results of these tests for a few representative species of the genus are shown in the tables, where A = 5-Methyl-6-(1'-p-methoxybenzoyl-benzotriazol-5'-yl)-4,5-dihydro-3(2H)-pyridazinone,
B = 5-Methyl-6-(1'-cyclohexanoyl-benzotriazol-5'-yl)-4,5-dihydro-3(2H)-pyridazinone,
C = 5-Methyl-6-(1'-isopropyl-benzotriazol-5'-yl)-4,5-dihydro-3(2H)-pyridazinone,
D = 5-Methyl-6-(1'-ethyl-benzotriazol-5'-yl)-4,5-dihydro-3(2H)-pyridazinone,
E = 5-Methyl-6-(1'-p-methoxybenzyl-benzotriazol-5'-yl)-4,5-dihydro-3(2H)-pyridazinone,
F = 5-Methyl-6-[1'-(2-dimethylaminoethyl)-benzotriazol-5'-yl]-4,5-dihydro-3(2H)-pyridazinone, and
G = 5-Methyl-6-(1'-methyl-benzotriazol-5'-yl)-4,5-dihydro-3(2H)-pyridazinone.

1.

Determination of the thrombocyte aggregation according to Born and Cross [J. Physiol. 170, 397 (1964)]

The thrombocyte aggregation was determined in platelet-rich plasma from healthy human test subjects. The course of decrease in optical density after the administration of standard commercial collagen (made by the Sigma Co., St. Louis, Mo.) containing 1 mg of collagen fibrils per ml was measured photometrically and recorded. The rate of aggregation ($V_{max}$) was deduced from the angle of inclination of the density curve. The point on the curve where there was most light transmittance was used to calculate the optical density (O.D.). To initiate maximum aggregation, about 0.01 ml of the collagen solution was added to 1 ml of platelet-rich plasma.

The following Table shows the results obtained:

| Compound | $EC_{50}$ in mol/liter |
| --- | --- |
| A | $2.7 \times 10^{-7}$ |
| B | $2.8 \times 10^{-7}$ |
| C | $3.3 \times 10^{-8}$ |
| D | $4.1 \times 10^{-8}$ |
| F | $3.0 \times 10^{-7}$ |
| G | $5.1 \times 10^{-8}$ |

2.

Determination of hypotensive and positive inotropic activity in the anesthetized cat The tests were carried out on cats which had been anesthetized with sodium pentobarbital (40 mg/kg i.p.). The animals breathed spontaneously. The arterial blood pressure was measured in the aorta abdominalis using a Statham pressure transducer (P 23 Dc). To determine the positive inotropic effect, the pressure in the left ventricle of the heart was measured using a catheter-tip manometer (Milliar PC-350 A). From this, the contractility parameter (dp/dt$_{max}$ was obtained by means of an analog differentiator.

The test compounds were injected into a vena femoralis. Physiological saline solution or Polydiol 200 was used as the solvent. Each compound was tested on at least 3 cats in a dosage of 0.1 or 2.0 mg/kg i.v. The duration of activity of the test compounds was at least 45 minutes in each case.

The following Table contains the average values:

| Compound | Dosage mg/kg i.v. | Change in blood pressure in mm Hg | Increase in dp/dt in % |
|---|---|---|---|
| A | 0.1 | −16/−16 | +105 |
| B | 2.0 | −60/−37 | +154 |
| C | 0.1 | −27/−33 | +116 |
| D | 0.1 | −30/−32 | +125 |
| E | 0.1 | −48/−48 | +167 |
| G | 0.1 | −33/−38 | +168 |

3.

Acute toxicity

In therapeutic doses the test substances are non-toxic. For example, compound B has a peroral LD$_{50}$ of >50 mg/kg in the mouse.

In view of their pharmacological properties, the compounds of the formula I, the optically active enantiomers thereof, and their non-toxic, pharmacologically acceptable addition salts with inorganic or organic acids are useful for the treatment of chronic cardiac insufficiency or angina pectoris and for the prophylaxis of arterial thromboembolism and arterial occlusion.

For pharmaceutical purpose the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds of the present inventions is from 0.14 to 0.71 mgm/kg, preferably 0.29 to 0.57 mgm/kg body weight i.v., and from 0.71 to 2.14 mgm/kg, preferably 1.07 to 1.43 mgm/kg body weight p.o., 1 to 4 times daily.

The following examples illustrate a few pharmaceutical compositions comprising a compound of the present invention as an active ingredient and represent the best modes contemplated of using the invention. The parts are parts by weight unless otherwise specified.

EXAMPLE 30

Tablets containing 100 mg of 5-methyl-6-(1'-methyl-benzotriazol-5'-yl)-4,5-dihydro-3(2H)-pyridazinone The tablet composition is compounded from the following ingredients:

| Active ingredient | 100.0 parts |
|---|---|
| Lactose | 50.0 parts |
| Polyvinyl pyrrolidone | 5.0 parts |
| Carboxymethylcellulose | 19.0 parts |
| Magnesium stearate | 1.0 parts |
| | 175.0 parts |

The active ingredient and lactose are mixed and homogeneously moistened with an aqueous solution of the polyvinyl pyrrolidone.
Moist screening: 1.5 mm-mesh
Drying: Circulating air drier at 50° C.
Dry-screening: 1 mm-mesh.
The remaining excipients are added to the granulate, and the finished mixture is compressed into tablets.
Weight of tablet: 175 mg
Punch: 8 mm φ.

EXAMPLE 31

Coated tablets containing 50 mg of 5-methyl-6-(1'-methylbenzotriazol-5'-yl)-4,5-dihydro-3(2H)-pyridazinone The tablet core composition is compounded from the following ingredients:

| Active ingredient | 50.0 parts |
|---|---|
| Dried corn starch | 20.0 parts |
| Soluble starch | 2.0 parts |
| Carboxymethylcellulose | 7.0 parts |
| Magnesium stearate | 1.0 parts |
| | 80.0 parts |

The active ingredient and starch are mixed and homogeneously moistened with an aqueous solution of the soluble starch.
Moist screening: 1.0 mm-mesh.
Drying: 50° C. in a circulating air drier.
Dry screening: 1.0 mm-mesh.
The granulate and remaining excipients are mixed together and compressed into tablet cores.
Weight of core: 80 mg
Punch: 6 mm
Radius of curvature: 5 mm.
The finished cores are coated with a sugar shell in a coating vessel in the usual way.
Weight of coated tablet: 120 mg.

EXAMPLE 32

Suppositories containing 75 mg of 5-methyl-6-(1'-methylbenzotriazol-5'-yl)-4,5-dihydro-3(2H)-pyridazinone The suppository composition is compounded from the following ingredients:

| Active ingredient | 75.0 parts |
|---|---|
| Suppository base (e.g. cocoa butter) | 1625.0 parts |
| | 1700.0 parts |

Preparation

The suppository base is melted. At 38° C. the ground active substance is homogeneously dispersed in the melt. It is then cooled to 35° C. and poured into precooled suppository molds.
Weight of suppository: 1.7 gm.

EXAMPLE 33

Hypodermic solution containing 25 mg of 5-methyl-6-(1'-methyl-benzotriazol-5'-yl)-4,5-dihydro-3(2H)-pyridazinone The solution was compounded from the following ingredients:

| | | |
|---|---|---|
| Active ingredient | 25.0 | parts |
| Sodium chloride | 45.0 | parts |
| Polyethyleneglycol 600 | 1000.0 | parts by vol. |
| Solubilizer (e.g. hydroxyethylated hydrogenated castor oil) | 500.0 | parts by vol. |
| Water for injection q.s. ad | 5000.0 | parts by vol. |

Preparation

In a suitable calibrated vessel, the active ingredient is dissolved in a mixture of polyethyleneglycol, solubilizer and about half the water, while stirring. After everything has dissolved, the sodium chloride is added, and the solution is made up to the stated volume with water.

EXAMPLE 34

Suspension containing 75 mg of 5-methyl-6-(1'-methylbenzotriazol-5'-yl)-4,5-dihydro-3(2H)-pyridazinone per 100 ml The suspension is compounded from the following ingredients:

| | | |
|---|---|---|
| Active ingredient | 1.5 | parts |
| Carboxymethylcellulose | 0.1 | parts |
| Methyl p-hydroxybenzoate | 0.05 | parts |
| Propyl p-hydroxybenzoate | 0.03 | parts |
| Sucrose | 10.0 | parts |
| Glycerol | 5.0 | parts |
| 70% sorbitol solution | 20.0 | parts |
| Flavoring | 0.3 | parts |
| Distilled water q.s.ad | 100.0 | parts by vol. |

Preparation

The distilled water is heated to 70° C. The methyl and propyl p-hydroxybenzoates and the glycerol and carboxymethyl-cellulose are dissolved therein by stirring. The solution is cooled to room temperature, and the active substance is added and homogeneously dispersed therein by stirring. After the sugar, sorbitol solution and flavoring have been added and dissolved, the suspension is evacuated, while stirring, to remove air.

Any one of the other compounds embraced by formula I or a non-toxic, pharmacologically acceptable acid addition salt thereof may be substituted for the particular active ingredient in Examples 30 through 34. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

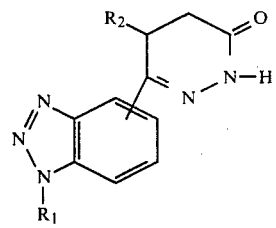

wherein
$R_1$ is α-monosubstituted alkyl of 2 to 4 carbon atoms, where the substituent is di(alkyl of 1 to 3 carbon atoms)amino, and
$R_2$ is hydrogen or alkyl of 1 to 3 carbon atoms;
or a non-toxic, pharmacologically acceptable addition salt thereof formed with an inorganic or organic acid.

2. A compound of claim 1, where
$R_1$ is α-monosubstituted alkyl of 2 to 4 carbon atoms, where the substituent is di(alkyl of 1 to 3 carbon atoms)amino, and
$R_2$ is methyl;
or a non-toxic, pharmacologically acceptable acid addition salt thereof.

3. A compound of claim 2, where the pyridazinone ring is attached to the 5-position of the benzotriazole moiety.

4. A compound of claim 1, which is 5-methyl-6-[1'-(2-dimethylamino-ethyl)-benzotriazol-5'-yl]-4,5-dihydro-3(2H)-pyridazinone or a non-toxic, pharmacologically acceptable addition salt thereof.

5. A compound of claim 1, which is 5-methyl-6-[1'-(3-di-n-propylamino-propyl)-benzotriazol-5'-yl]-4,5-dihydro-3(2H)pyridazinone or a non-toxic, pharmacologically acceptable addition salt thereof.

6. A cardiotonic, hypotensive or antithrombotic pharmaceutical composition consisting essentially of an inert pharmaceutical carrier and an effective cardiotonic, hypotensive or anthithrombotic amount of a compound of claim 1.

7. The method of strengthening the action of the heart, lowering the blood pressure or preventing or relieving thromboses is a warm-blooded animal in need thereof, which comprises perorally, parenterally or rectally administering to said animal an effective cardiotonic, hypotensive or antithrombotic amount of a compound of claim 1.

* * * * *

UNITED STATES PATENT AND TRADEMARK OFFICE
CERTIFICATE OF CORRECTION

PATENT NO. : 4,699,909

DATED : October 13, 1987

INVENTOR(S) : NORBERT HAUEL ET AL.

It is certified that error appears in the above-identified patent and that said Letters Patent is hereby corrected as shown below:

Title page, [30] Foreign Application Priority Data:

"129447" should read -- 3129447 --.

Column 2, line 29: "$\alpha$-monosubstituted" should read

-- $\omega$-monosubstituted --.

Signed and Sealed this

Third Day of May, 1988

Attest:

DONALD J. QUIGG

Attesting Officer

Commissioner of Patents and Trademarks